US008968292B2

(12) United States Patent
Rossetto et al.

(10) Patent No.: US 8,968,292 B2
(45) Date of Patent: *Mar. 3, 2015

(54) LEAKY-WAVE ANTENNAS FOR MEDICAL APPLICATIONS

(71) Applicant: Covidien LP, Mansfield, MA (US)

(72) Inventors: Francesca Rossetto, Longmont, CO (US); Joseph D. Brannan, Erie, CO (US); Joseph A. Paulus, Louisville, CO (US); Christopher A. Deborski, Denver, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/192,142

(22) Filed: Feb. 27, 2014

(65) Prior Publication Data

US 2014/0180270 A1 Jun. 26, 2014

Related U.S. Application Data

(63) Continuation of application No. 13/483,858, filed on May 30, 2012, now Pat. No. 8,679,108, which is a continuation of application No. 12/389,906, filed on Feb. 20, 2009, now Pat. No. 8,197,473.

(51) Int. Cl.
*A61B 18/04* (2006.01)
*A61B 18/18* (2006.01)
(Continued)

(52) U.S. Cl.
CPC ............. *A61B 18/18* (2013.01); *A61B 18/1815* (2013.01); *H01Q 1/273* (2013.01); *H01Q 13/203* (2013.01); *H04B 5/0018* (2013.01)

USPC .......................................................... 606/33

(58) Field of Classification Search
CPC .. A61B 18/18; A61B 18/1815; H04B 5/0018; H01Q 13/203; H01Q 1/273
USPC ......... 604/21, 22; 606/45, 39, 33; 607/99, 116
See application file for complete search history.

(56) References Cited

U.S. PATENT DOCUMENTS 2,480,181 A 8/1949 Breen
2,601,610 A 6/1952 Hatch
(Continued)

FOREIGN PATENT DOCUMENTS

CN 1103807 A 6/1995
DE 390937 C 3/1924
(Continued)

OTHER PUBLICATIONS

European Search Report EP 06014461.5 dated Oct. 31, 2006.
(Continued)

*Primary Examiner* — Manuel Mendez

(57) ABSTRACT

A device for directing energy to a target volume of tissue includes an inner conductor having a length and an outer conductor coaxially surrounding the inner conductor along the length. The outer conductor has a proximal portion and a distal portion. The distal portion of the outer conductor is provided with a number of apertures N defined therein for radiating energy, where N is an integer greater than 1, each aperture having a size and extending at an angle relative to a longitudinal axis of the outer conductor. At least one of the size and the angle of each aperture is varied in relation to the other apertures N-1 such that the energy radiated along the distal portion is substantially uniform.

20 Claims, 9 Drawing Sheets

(51) Int. Cl.
    *H01Q 1/27* (2006.01)
    *H01Q 13/20* (2006.01)
    *H04B 5/00* (2006.01)

(56) References Cited

U.S. PATENT DOCUMENTS

| | | |
|---|---|---|
| 3,631,363 A | 12/1971 | Miller |
| 3,795,915 A | 3/1974 | Yoshida |
| 3,870,977 A | 3/1975 | Peoples et al. |
| 4,316,474 A | 2/1982 | Spethmann |
| 4,397,313 A | 8/1983 | Vaguine |
| 4,448,198 A | 5/1984 | Turner |
| 4,462,412 A | 7/1984 | Turner |
| 4,572,190 A | 2/1986 | Azam et al. |
| 4,700,716 A | 10/1987 | Kasevich et al. |
| 4,798,215 A | 1/1989 | Turner |
| 4,841,988 A | 6/1989 | Fetter et al. |
| 4,901,253 A | 2/1990 | Iwano et al. |
| 4,934,365 A | 6/1990 | Morgenthaler |
| 4,974,587 A | 12/1990 | Turner et al. |
| 5,026,959 A | 6/1991 | Ito et al. |
| 5,057,106 A | 10/1991 | Kasevich et al. |
| 5,097,844 A | 3/1992 | Turner |
| 5,097,845 A | 3/1992 | Fetter et al. |
| 5,190,054 A | 3/1993 | Fetter et al. |
| 5,343,410 A | 8/1994 | Tsujiuchi et al. |
| 5,364,336 A | 11/1994 | Carr |
| 5,405,346 A | 4/1995 | Grundy et al. |
| 5,417,210 A | 5/1995 | Funda et al. |
| 5,579,246 A | 11/1996 | Ebersbach et al. |
| 5,800,378 A | 9/1998 | Edwards et al. |
| 5,800,494 A | 9/1998 | Campbell et al. |
| 5,921,982 A | 7/1999 | Lesh et al. |
| 6,031,375 A | 2/2000 | Atalar et al. |
| 6,375,606 B1 | 4/2002 | Garibaldi et al. |
| 6,412,329 B1 | 7/2002 | Nai |
| 6,451,015 B1 | 9/2002 | Rittman, III et al. |
| 6,603,994 B2 | 8/2003 | Wallace et al. |
| 6,640,139 B1 | 10/2003 | Ueberle |
| 6,677,901 B1 | 1/2004 | Nalbandian |
| 6,725,080 B2 | 4/2004 | Melkent et al. |
| 7,070,597 B2 | 7/2006 | Truckai et al. |
| 7,118,590 B1 | 10/2006 | Cronin |
| 7,286,949 B2 | 10/2007 | McFarland et al. |
| 7,387,627 B2 | 6/2008 | Erb et al. |
| 7,439,736 B2 | 10/2008 | Meaney et al. |
| 7,467,015 B2 | 12/2008 | van der Weide |
| 7,565,207 B2 | 7/2009 | Turner et al. |
| 7,642,451 B2 | 1/2010 | Bonn |
| 7,875,024 B2 | 1/2011 | Turovskiy et al. |
| 7,998,139 B2 | 8/2011 | Rossetto et al. |
| 8,035,570 B2 | 10/2011 | Prakash et al. |
| 8,059,059 B2 | 11/2011 | Bonn |
| 8,118,808 B2 | 2/2012 | Smith et al. |
| 8,182,480 B2 | 5/2012 | Huseman |
| 8,192,427 B2 | 6/2012 | Buysse |
| 8,197,473 B2 * | 6/2012 | Rossetto et al. ............... 606/33 |
| 8,202,270 B2 | 6/2012 | Rossetto et al. |
| 8,211,098 B2 | 7/2012 | Paulus |
| 8,211,099 B2 | 7/2012 | Buysse et al. |
| 8,216,227 B2 | 7/2012 | Podhajsky |
| 8,221,418 B2 | 7/2012 | Prakash et al. |
| 8,235,981 B2 | 8/2012 | Prakash et al. |
| 8,246,614 B2 | 8/2012 | DeCarlo |
| 8,251,987 B2 | 8/2012 | Willyard |
| 8,262,703 B2 | 9/2012 | Prakash et al. |
| 8,679,108 B2 * | 3/2014 | Rossetto et al. ............... 606/33 |
| 2002/0022836 A1 | 2/2002 | Goble et al. |
| 2002/0149533 A1 | 10/2002 | Toncich |
| 2002/0183964 A1 | 12/2002 | Handa et al. |
| 2003/0014046 A1 | 1/2003 | Edwards et al. |
| 2003/0032951 A1 | 2/2003 | Rittman et al. |
| 2003/0078573 A1 | 4/2003 | Truckai et al. |
| 2003/0144658 A1 | 7/2003 | Schwartz et al. |
| 2004/0044385 A1 | 3/2004 | Fenn et al. |
| 2004/0097805 A1 | 5/2004 | Verard et al. |
| 2004/0133254 A1 | 7/2004 | Sterzer et al. |
| 2004/0242992 A1 | 12/2004 | Hareyama |
| 2006/0293651 A1 | 12/2006 | Cronin |
| 2008/0266203 A1 | 10/2008 | Rossetto et al. |
| 2009/0054888 A1 | 2/2009 | Cronin |
| 2009/0138005 A1 | 5/2009 | Prakash et al. |
| 2009/0187180 A1 | 7/2009 | Brannan |
| 2009/0192510 A1 | 7/2009 | Bahney |
| 2009/0198227 A1 | 8/2009 | Prakash |
| 2009/0222002 A1 | 9/2009 | Bonn et al. |
| 2009/0248005 A1 | 10/2009 | Rusin et al. |
| 2009/0248006 A1 | 10/2009 | Paulus et al. |
| 2009/0306652 A1 | 12/2009 | Buysse et al. |
| 2009/0326620 A1 | 12/2009 | Rossetto et al. |
| 2010/0030206 A1 | 2/2010 | Brannan et al. |
| 2010/0030208 A1 | 2/2010 | Manley |
| 2010/0030210 A1 | 2/2010 | Paulus |
| 2010/0045558 A1 | 2/2010 | Rossetto |
| 2010/0045559 A1 | 2/2010 | Rossetto |
| 2010/0057070 A1 | 3/2010 | Behnke et al. |
| 2010/0076422 A1 | 3/2010 | Podhajsky |
| 2010/0087808 A1 | 4/2010 | Paulus |
| 2010/0094272 A1 | 4/2010 | Rossetto et al. |
| 2010/0094273 A1 | 4/2010 | Rossetto et al. |
| 2010/0097284 A1 | 4/2010 | Brannan et al. |
| 2010/0256624 A1 | 10/2010 | Brannan et al. |
| 2010/0262134 A1 | 10/2010 | Jensen et al. |
| 2010/0286681 A1 | 11/2010 | Podhajsky |
| 2010/0286683 A1 | 11/2010 | Podhajsky |
| 2010/0305559 A1 | 12/2010 | Brannan et al. |
| 2010/0305560 A1 | 12/2010 | Peterson |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0 246 350 A1 | 11/1987 |

(56) References Cited

FOREIGN PATENT DOCUMENTS

| | | | |
|---|---|---|---|
| EP | 0 481 685 A1 | 4/1992 | |
| EP | 0 521 264 A2 | 1/1993 | |
| EP | 0 556 705 A1 | 8/1993 | |
| EP | 0 558 429 A1 | 9/1993 | |
| EP | 0572131 A1 | 12/1993 | |
| EP | 0 648 515 A1 | 4/1995 | |
| EP | 0541930 B1 | 3/1998 | |
| EP | 0 836 868 A2 | 4/1998 | |
| EP | 0 882 955 A1 | 12/1998 | |
| EP | 1 159 926 A2 | 12/2001 | |
| EP | 1278007 | 1/2003 | |
| EP | 1186274 | 4/2006 | |
| EP | 1 810 627 A1 | 7/2007 | |
| FR | 179 607 | 11/1906 | |
| FR | 1 275 415 A | 11/1961 | |
| FR | 1 347 865 A | 1/1964 | |
| FR | 2 235 669 A1 | 1/1975 | |
| FR | 2 276 027 A1 | 1/1976 | |
| FR | 2 313 708 A1 | 12/1976 | |
| FR | 2 502 935 A1 | 10/1982 | |
| FR | 2 517 953 A1 | 6/1983 | |
| FR | 2 573 301 A1 | 5/1986 | |
| FR | 2 862 813 A1 | 5/2005 | |
| FR | 2 864 439 A1 | 7/2005 | |
| GB | 1321582 A | 6/1973 | |
| GB | 2434872 A | 8/2007 | |
| JP | 5-5106 | 1/1993 | |
| JP | 05-40112 | 2/1993 | |
| JP | 06343644 A | 12/1994 | |
| JP | 07265328 A | 10/1995 | |
| JP | 08056955 A | 3/1996 | |
| JP | 08252263 A | 10/1996 | |
| JP | 09000492 A | 1/1997 | |
| JP | 09010223 A | 1/1997 | |
| JP | 11244298 A | 9/1999 | |
| JP | 2000342599 A | 12/2000 | |
| JP | 2000350732 A | 12/2000 | |
| JP | 2001003776 A | 1/2001 | |
| JP | 2001008944 A | 1/2001 | |
| JP | 2001029356 A | 2/2001 | |
| JP | 2001037775 A | 2/2001 | |
| JP | 2001128990 A | 5/2001 | |
| JP | 2001231870 A | 8/2001 | |
| JP | 2008142467 A | 6/2008 | |
| SU | 166452 | 11/1964 | |
| SU | 401367 A1 | 10/1973 | |
| SU | 727201 A2 | 4/1980 | |
| WO | 9505869 A1 | 3/1995 | |
| WO | 97/41924 A1 | 11/1997 | |
| WO | 97/43971 A2 | 11/1997 | |
| WO | 00/36985 A2 | 6/2000 | |
| WO | 00/48672 A1 | 8/2000 | |
| WO | 00/51513 A1 | 9/2000 | |
| WO | 01/01847 | 1/2001 | |
| WO | 01/74252 A2 | 10/2001 | |
| WO | 02/45790 A2 | 6/2002 | |
| WO | 02/061880 A2 | 8/2002 | |
| WO | 2004084748 A1 | 10/2004 | |
| WO | 2004/112628 A1 | 12/2004 | |
| WO | 2005/016119 A2 | 2/2005 | |
| WO | 2010/035831 A1 | 4/2010 | |

OTHER PUBLICATIONS

European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08015842 dated Dec. 5, 2008.
European Search Report EP 98300964.8 dated Dec. 13, 2000.
European Search Report EP 98944778 dated Nov. 7, 2000.
European Search Report EP 98958575.7 dated Oct. 29, 2002.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US98/18640 dated Jan. 29, 1998.
International Search Report PCT/US98/23950 dated Jan. 14, 1998.
International Search Report PCT/US99/24869 dated Feb. 11, 2000.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/343,788, filed Jan. 5, 2012, William O. Reid, Jr.
U.S. Appl. No. 13/343,798, filed Jan. 5, 2012, William O. Reid, Jr.
U.S. Appl. No. 13/344,753, filed Jan. 6, 2012, Lee et al.
U.S. Appl. No. 13/344,790, filed Jan. 6, 2012, Lee et al.
U.S. Appl. No. 13/400,223, filed Feb. 20, 2012, Anthony B. Ross.
U.S. Appl. No. 13/419,981, filed Mar. 14, 2012, Joseph D. Brannan.

(56) References Cited

OTHER PUBLICATIONS

U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,307, filed May 22, 2012, Casey M. Ladtkow.
U.S. Appl. No. 13/477,320, filed May 22, 2012, Joseph D. Brannan.
U.S. Appl. No. 13/483,858, filed May 30, 2012, Francesca Rossetto.
U.S. Appl. No. 13/488,964, filed Jun. 5, 2012, Steven P. Buysse.
U.S. Appl. No. 13/525,853, filed Jun. 18, 2012, Joseph A. Paulus.
U.S. Appl. No. 13/526,676, filed Jun. 19, 2012, Francesca Rossetto.
U.S. Appl. No. 13/539,650, filed Jul. 2, 2012, Joseph A. Paulus.
U.S. Appl. No. 13/539,690, filed Jul. 2, 2012, Steven P. Buysse.
U.S. Appl. No. 13/539,725, filed Jul. 2, 2012, Steven P. Buysse.
U.S. Appl. No. 13/539,875, filed Jul. 2, 2012, Mani N. Prakash.
U.S. Appl. No. 13/551,005, filed Jul. 17, 2012, Chris Rusin.
U.S. Appl. No. 13/567,624, filed Aug. 6, 2012, Mani N. Prakash.
U.S. Appl. No. 13/568,679, filed Aug. 7, 2012, Robert J. Behnke, II.
U.S. Appl. No. 13/596,785, filed Aug. 28, 2012, Richard A. Willyard.
U.S. Appl. No. 13/598,141, filed Aug. 29, 2012, Kenlyn S. Bonn.
Cosman et al., "Methods of Making Nervous System Lesions" in William RH, Rengachary SS (eds): Neurosurgery, New York: McGraw.cndotHill, vol. 111, (1984), pp. 2490-2499.
Esterline, "Light Key Projection Keyboard" Advanced Input Systems, located at: <http://www.advanced-input.com/lightkey> 2002.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Humphries Jr. et al., "Finite Element Codes to Model Electrical Heating and Non.cndot.LInear Thermal Transport in Biological Media", Proc. ASME HTD-355, 131 (1997).
Johnson et al., "New Low-Profile Applicators for Local Heating of Tissues", IEEE Transactions on Biomedical Engineering, vol. BME-31, No. 1, Jan. 1984, pp. 28-37.
Livraghi et al., (1995) "Saline-enhanced RF Tissue Ablation in the Treatment of Liver Metastases", Radiology, p. 140 (Abstr).
Ni Wei et al., "A Signal Processing Method for the Coriolis Mass Flowmeter Based on a Normalized . . . " Journal of Applied Sciences. cndot. Yingyong Kexue Xuebao, Shangha CN, vol. 23, No. 2:(Mar. 2005); pp. 160-184.
Solbiati et al. (1995) "Percutaneous US-guided RF Tissue Ablation of Liver Metastases: Long-term Follow-up", Radiology, pp. 195-203.
T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis.TM. Technology (Date Unknown). "Overcoming the Challenge" located at: <http://www.urologix.com!medicaUtechnology.html > Nov. 18, 1999; 3 pages.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 02786604.5 dated Feb. 10, 2010.
European Search Report EP 06006963 dated Aug. 4, 2006.
European Search Report EP 07015191.5 dated Jan. 23, 2008.
European Search Report EP 07015601.3 dated Jan. 4, 2008.
European Search Report EP 08001016.8 dated Jan. 4, 2008.
European Search Report EP 08004974.5 dated Apr. 6, 2011.
European Search Report EP 08007924.7 partial dated Aug. 17, 2010.
European Search Report EP 08011705.4 extended dated Nov. 4, 2009.
European Search Report EP 08020530.5 dated May 27, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09161502.1 extended dated Oct. 30, 2009.
European Search Report EP 09165976.3 extended dated Mar. 17, 2010.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Oct. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009392.1 extended dated Sep. 19, 2011.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11000669.9 extended dated Jun. 30, 2011.
European Search Report EP 11001596.3 extended dated Jul. 4, 2011.
European Search Report EP 11001872.8 extended dated Jul. 6, 2011.
European Search Report EP 11004942 dated Oct. 4, 2011.

(56) References Cited

OTHER PUBLICATIONS

European Search Report EP 11009036.2 dated Feb. 13, 2012.
European Search Report EP 11010024.5 dated Apr. 20, 2012.
European Search Report EP 11010046.8 dated Apr. 17, 2012.
European Search Report EP 11010093.0 dated Mar. 27, 2012.
European Search Report EP 11010175.5 dated May 10, 2012.
European Search Report EP 11010176.3 dated Apr. 2, 2012.
European Search Report EP 11010177.1 dated May 10, 2012.
European Search Report EP 11174318.3 dated Nov. 7, 2011.
European Search Report EP 11185926.0 dated Feb. 3, 2012.
European Search Report EP 12000334.8 dated May 4, 2012.
European Search Report EP 12000335.5 dated May 10, 2012.
European Search Report EP 12000336.3 dated May 14, 2012.
European Search Report EP 12001841.1 dated Jul. 16, 2012.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US04/15311 dated Jan. 12, 2005.
International Search Report PCT/US10/032796 dated Jul. 28, 2010.
European Search Report dated Oct. 9, 2013 in European Application No. 13004127.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
U.S. Appl. No. 12/401,268, filed Mar. 10, 2009.
U.S. Appl. No. 12/413,011, filed Mar. 27, 2009.
U.S. Appl. No. 12/413,023, filed Mar. 27, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/434,903, filed May 4, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure.TM. Vessel Sealing System in Abdominal Surgery" Innovations That Work, Jun. 2002.

(56) References Cited

OTHER PUBLICATIONS

Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Cosman et al., "Methods of Making Nervous System Lesions" In William RH, Rengachary SS (eds): Neurosurgery, New York: McGraw Hill, vol. 111, (1984), pp. 2490-2499.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline Product Literature, "Light Key: Visualize a Virtual Keyboard. One With No Moving Parts", 4 pages.
Esterline, "Light Key Projection Keyboard" 2004 Advanced Input Systems, located at: <http://www.advanced-input.com/lightkey> last visited on Feb. 10, 2005.
Geddes et al., "The Measurement of Physiologic Events by Electrical Impedence" Am. J. MI, Jan. Mar. 1964, pp. 16-27.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Johnson et al., "Evaluation of a Bipolar Electrothermal Vessel Sealing Device in Hemorrhoidectomy" Sales/Product Literature, Jan. 2004.
Jarrett et al., "Use of the LigaSure.TM. Vessel Sealing System for Peri-Hilar Vessels in Laparoscopic Nephrectomy" Sales/Product Literature 2000.
Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Intl Federation of Gynecology and Obstetrics FIGO World Congress 2000, Washington, DC.
MDTECH product literature (Mar. 2000) I'D Wire: product description, 1 page.
MDTECH product literature (Dec. 1999) "FlexStrand": product description, 1 page.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2: Mar. 2005 pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.

(56) References Cited

OTHER PUBLICATIONS

Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
S. Humphries Jr. et al., "Finite.cndot.Element Codes to Model Electrical Heating and Non.cndot.LInear Thermal Transport in Biological Media", Proc. ASME HTD-355, 131 (1997).
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
Esterline Product Literature, "Light Key: Visualize a Virtual Keyboard. One With No Moving Parts", Nov. 1, 2003; 4 pages.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

European Search Report EP 08011282 dated Aug. 14, 2009.
European Search Report EP 04778192.7 dated Jul. 1, 2009.
European Search Report EP 05810523 dated Jan. 29, 2009.
European Search Report EP 08011705 dated Aug. 20, 2009.
European Search Report EP 08012829.1 dated Oct. 29, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report EP 10001767 dated Jun. 18, 2010.
U.S. Appl. No. 08/483,742, filed Jun. 7, 1995.
U.S. Appl. No. 08/136,098, filed Oct. 14, 1993.
U.S. Appl. No. 09/195,118, filed Nov. 18, 1998.
U.S. Appl. No. 10/244,346, filed Sep. 16, 2002.
U.S. Appl. No. 11/053,987, filed Feb. 8, 2005.
U.S. Appl. No. 12/023,606, filed Jan. 31, 2008.
U.S. Appl. No. 12/129,482, filed May 29, 2008.
U.S. Appl. No. 12/135,425, filed Jun. 9, 2008.
U.S. Appl. No. 12/135,690, filed Jun. 9, 2008.
U.S. Appl. No. 12/147,093, filed Jun. 26, 2008.
U.S. Appl. No. 12/181,504, filed Jul. 29, 2008.
U.S. Appl. No. 12/184,556, filed Aug. 1, 2008.
U.S. Appl. No. 12/194,254, filed Aug. 19, 2008.
U.S. Appl. No. 12/197,601, filed Aug. 25, 2008.
U.S. Appl. No. 12/197,405, filed Aug. 25, 2008.
U.S. Appl. No. 12/197,473, filed Aug. 25, 2008.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 3, 2008.
U.S. Appl. No. 12/250,110, filed Oct. 13, 2008.
U.S. Appl. No. 12/250,171, filed Oct. 13, 2008.
U.S. Appl. No. 12/253,457, filed Oct. 17, 2008.
U.S. Appl. No. 12/277,951, filed Nov. 25, 2008.
U.S. Appl. No. 12/350,292, filed Jan. 8, 2009.
U.S. Appl. No. 12/351,633, filed Jan. 9, 2009.
U.S. Appl. No. 12/353,623, filed Jan. 14, 2009.
U.S. Appl. No. 12/353,617, filed Jan. 14, 2009.
U.S. Appl. No. 12/356,650, filed Jan. 21, 2009.
U.S. Appl. No. 12/366,298, filed Feb. 5, 2009.
U.S. Appl. No. 12/389,906, filed Feb. 20, 2009.
U.S. Appl. No. 12/389,915, filed Feb. 20, 2009.
U.S. Appl. No. 12/395,034, filed Feb. 27, 2009.
U.S. Appl. No. 12/399,222, filed Mar. 6, 2009.

* cited by examiner

LEAKY-WAVE ANTENNAS FOR MEDICAL APPLICATIONS

CROSS-REFERENCE TO RELATED APPLICATIONS

The present application is a continuation application of U.S. application Ser. No. 13/483,858, filed May 30, 2012, which is a continuation application of U.S. application Ser. No. 12/389,906, filed May 20, 2009, now U.S. Pat. No. 8,197,473, the entire contents of all of which are incorporated by reference herein.

BACKGROUND

1. Technical Field

The present disclosure relates to antennas and, more particularly, to electrosurgical devices with leaky-wave antenna assemblies suitable for use in tissue ablation applications.

2. Discussion of Related Art

Treatment of certain diseases requires the destruction of malignant tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of cancer cells have been found to denature at elevated temperatures that are slightly lower than temperatures normally injurious to healthy cells. Known treatment methods, such as hyperthermia therapy, use electromagnetic radiation to heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of apparatus that can be used to perform ablation procedures. Typically, microwave apparatus for use in ablation procedures include a microwave generator, which functions as an energy source, and a microwave surgical instrument having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

Microwave energy is typically applied via antenna assemblies that can penetrate tissue. Several types of microwave antenna assemblies are known, such as monopole, dipole and helical. In monopole and dipole antenna assemblies, microwave energy generally radiates perpendicularly away from the axis of the conductor. A monopole antenna assembly includes a single, elongated conductor that transmits microwave energy. A typical dipole antenna assembly has two elongated conductors, which are linearly aligned and positioned end-to-end relative to one another with an electrical insulator placed therebetween. Helical antenna assemblies have two main modes of operation: normal mode (broadside) and axial mode (endfire). In the normal mode of operation, the field radiated by the helix is maximum in a perpendicular plane to the helix axis. In the axial mode, maximum radiation is along the helix axis.

A typical microwave transmission line assembly has a long, thin inner conductor that extends along a longitudinal transmission line axis and is surrounded by a dielectric material and is further surrounded by an outer conductor around the dielectric material such that the outer conductor also extends along the transmission line axis. In one variation of an antenna, the outer conductor is provided with a plurality of slots along a length of transmission line. This type of construction is typically referred to as a "leaky coaxial" or "leaky wave" antenna. A leaky wave antenna is basically a waveguiding structure constructed so as to "leak" power along the length of the guiding structure. In a leaky-wave antenna, as the microwave signal propagates inside the guiding structure (i.e., transmission line or coaxial cable), it "leaks" out through openings in the outer conductor, causing radiation.

Examples of leaky coaxial antennas include loose braid coaxial cables and slotted coaxial cables, which are sometimes used for communications applications such as, for example, transmitting and receiving signals within tunnels or buildings. A typical loose braid coaxial cable is shown in FIG. 1 and includes an inner conductor 120, an outer conductor 150 coaxially surrounding the inner conductor 120, and a dielectric material 140 separating the inner and outer conductors. The direction of the radiation pattern of the loose braid coaxial cable is indicated by the curved arrows in FIG. 1. An example of a slotted coaxial cable is illustrated in FIG. 2 and includes a central conductor 220, a cylindrical outer conductor 260, which is provided with a plurality of elongated slots 201A, 201B and 201C, and a dielectric material 240 separating the inner and outer conductors. In the slotted coaxial cable illustrated in FIG. 2, the slots 201A, 201B and 201C longitudinally extend along the longitudinal axis of the inner conductor 220. In the slotted coaxial cable shown in FIG. 3, a plurality of slots 301A, 301B and 301C are formed in the outer conductor 360 such that the longitudinal axis of each slot extends perpendicular to the longitudinal axis of the central conductor 320.

During certain procedures, it can be difficult to assess the extent to which the microwave energy will radiate into the surrounding tissue, making it difficult to determine the area or volume of surrounding tissue that will be ablated.

SUMMARY

The present disclosure relates to a device for directing energy to a target volume of tissue including an inner conductor having a length and an outer conductor coaxially surrounding the inner conductor along the length. The outer conductor has a proximal portion and a distal portion. The distal portion of the outer conductor is provided with a number of apertures N defined therein for radiating energy, where N is an integer greater than 1, each aperture having a size and extending at an angle relative to a longitudinal axis of the outer conductor. At least one of the size and the angle of each aperture is varied in relation to the other apertures N−1 such that the energy radiated along the distal portion is substantially uniform.

The present disclosure also relates to a system for directing energy to a target volume of tissue including a leaky-wave antenna assembly that includes an inner conductor and an outer conductor, each extending therethrough, wherein the inner conductor is disposed within the outer conductor. A distal portion of the outer conductor is provided with a number of apertures N defined therein for radiating energy, where N is an integer greater than 1, each aperture having a size and extending at an angle relative to a longitudinal axis of the outer conductor, wherein at least one of the size and the angle of each aperture is varied in relation to the other apertures N−1 such that the energy radiated along the distal portion is substantially the same.

The present disclosure also relates to a method for directing energy to a target volume of tissue including the step of positioning a leaky-wave antenna assembly for delivery of energy to the target volume of tissue. The method also includes the steps of: transmitting energy from an energy source to the leaky-wave antenna assembly; and applying the energy through a plurality of radiating apertures defined in a distal portion of the leaky-wave antenna assembly, the radiating apertures configured for radiating energy substantially uniformly along the longitudinal axis of the leaky-wave antenna assembly.

BRIEF DESCRIPTION OF THE DRAWINGS

Objects and features of the presently disclosed leaky-wave antenna assemblies will become apparent to those of ordinary skill in the art when descriptions of various embodiments thereof are read with reference to the accompanying drawings, of which.

DETAILED DESCRIPTION

Figure 1:
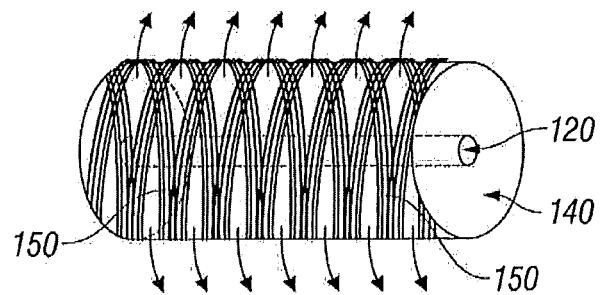
FIG. 1 is a perspective view of a prior art loose braid coaxial cable.
Figure 2:
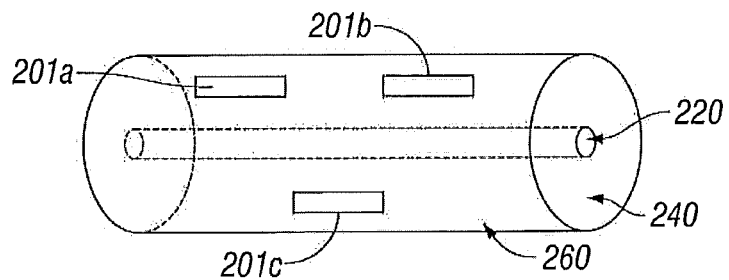
FIG. 2 is a perspective view of a prior art slotted coaxial cable.
Figure 3:
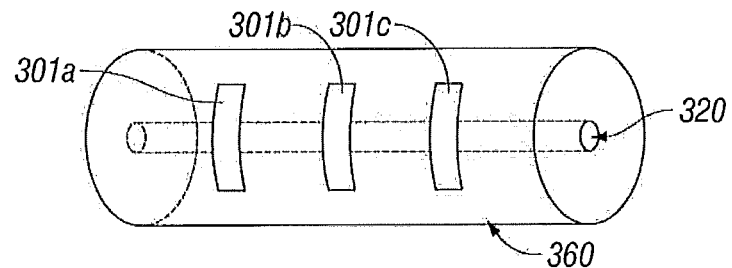
FIG. 3 is a perspective view of another prior art slotted coaxial cable.

Hereinafter, embodiments of the presently disclosed leaky-wave antenna assemblies will be described with reference to the accompanying drawings. Like reference numerals may refer to similar or identical elements throughout the description of the figures.

Electromagnetic energy is generally classified by increasing energy or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As used herein, the phrase "ablation procedure" generally refers to any ablation procedure, such as microwave ablation or microwave ablation assisted resection. As used herein, the phrase "transmission line" generally refers to any transmission medium that can be used for the propagation of signals from one point to another.

Various embodiments of the present disclosure provide electrosurgical devices for treating tissue and methods of directing electromagnetic radiation to a target volume of tissue. Embodiments may be implemented using electromagnetic radiation at microwave frequencies or at other frequencies. A leaky-wave antenna assembly, according to various embodiments, is capable of radiating energy substantially uniformly along the longitudinal axis of the leaky-wave antenna assembly. Multiple leaky-wave antenna assemblies can be employed in variously arranged configurations. For example, multiple leaky-wave antenna assemblies can be placed parallel to each other to substantially simultaneously ablate a target volume of tissue.

Various embodiments of the presently disclosed leaky-wave antenna assembly are suitable for microwave ablation and for use to pre-coagulate tissue for microwave ablation assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue.

Figure 4:
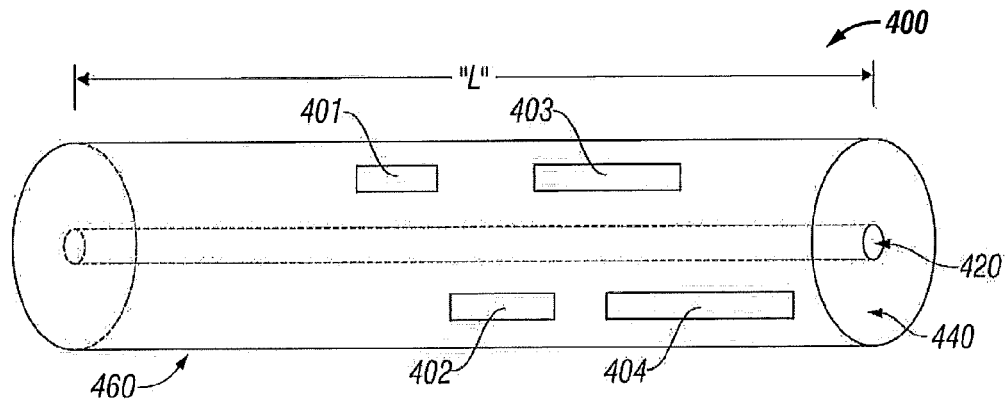
FIG. 4 is a perspective view of a leaky-wave antenna assembly according to an embodiment of the present disclosure.

FIG. 4 shows a leaky-wave antenna assembly according to an embodiment of the present disclosure. Referring to FIG. 4, the leaky-wave antenna assembly 400 includes an inner conductor 420 having a length "L" and an outer conductor 460 coaxially surrounding the inner conductor 420 along the length "L". Leaky-wave antenna assembly 400 may include a dielectric material 440 separating the inner conductor 420 and outer conductor 460. Dielectric material 440 may include ceramics, water, mica, polyethylene, glass, or metal oxides. Leaky-wave antenna assembly 400 may include an electrical short element (not shown) located at the distal end of the device for electrically connecting the inner conductor 420 and the outer conductor 460, such as a solder cap, metal plate or wire.

The distal portion of the outer conductor 460 is provided with a plurality of apertures for radiating energy. The apertures are configured for radiating energy substantially uniformly along the longitudinal axis of the distal portion of the outer conductor 460, e.g., to provide uniform ablation to the target tissue volume surrounding the leaky-wave antenna assembly 400.

In the leaky-wave antenna assembly 400 shown in FIG. 4, the sizes of the respective apertures are based on the location of each aperture relative to a distal tip of the leaky-wave antenna assembly 400. The number, shape, size, angle and relative spacing of the apertures may be varied from the configuration depicted in FIG. 4. In the illustrated embodiment, each of the apertures (referred to herein as slots 401, 402, 403 and 404) has a different size and longitudinally extends parallel to the longitudinal axis of the central conductor 420. Slots 401, 402, 403 and 404 are disposed in increasing order of size along the length of the distal portion of the outer conductor 460, which may increase radiation, since larger slots generally perturb currents more.

Leaky-wave antenna assembly 400 may be axially rigid to allow for tissue penetration. Leaky-wave antenna assembly 400 may be sufficiently small in diameter to be minimally invasive of the body, which may reduce the preparation time of the patient as might be required for more invasive penetration of the body. Leaky-wave antenna assembly 400 may include a tip portion that is advantageously dimensioned and shaped to facilitate penetration of tissue. The proximal end of the leaky-wave antenna assembly 400 may be coupled to a transmission line that electrically connects the leaky-wave antenna assembly 400 to a microwave energy source.

Figure 5:
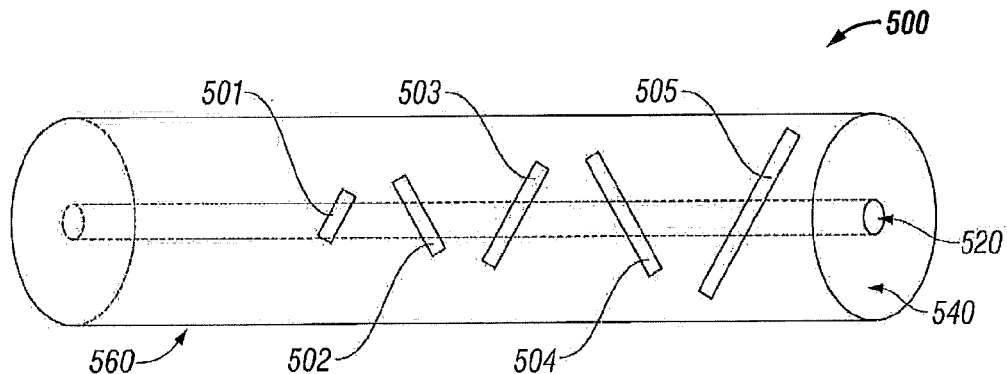
FIG. 5 is a perspective view of another embodiment of a leaky-wave antenna assembly according to the present disclosure.

FIG. 5 shows another embodiment of a leaky-wave antenna assembly. Leaky-wave antenna assembly 500 shown in FIG. 5 includes an inner conductor 520 and an outer conductor 560 coaxially surrounding the inner conductor 520, and may include a dielectric material 540 separating the inner conductor 520 and the outer conductor 560. Dielectric material 540 may include ferroelectric dielectric materials. The distal portion of the outer conductor 560 is provided with a plurality of apertures for radiating energy. The apertures are configured for radiating energy substantially uniformly along the longitudinal axis of the distal portion of the outer conductor 560. In the leaky-wave antenna assembly 500, radiation can be increased by placing each aperture in a position that causes high perturbation of the currents inside the guiding structure, i.e., transversal to the current lines, so that a high number of current lines is cut and perturbed by the apertures.

The sizes of the respective apertures and the leaky-wave antenna assembly 500 are based on at least one of the location of each aperture relative to a distal tip of the leaky-wave antenna assembly 500 and the angle of each aperture relative to the longitudinal axis of the central conductor 520. The number, shape, size, angle and relative spacing of the apertures may be varied from the configuration depicted in FIG. 5. In one embodiment, the energy radiated from each of the apertures is substantially the same.

In the leaky-wave antenna assembly 500 shown in FIG. 5, the apertures (referred to herein as the first, second, third, fourth and fifth slots 501, 502, 503, 504 and 505, respectively) each have a different size. In this embodiment, the first, second, third, fourth and fifth slots 501, 502, 503, 504 and 505 are positioned along the distal portion of the outer conductor 560 in order of increasing size, such that the first slot 501, which is the smallest opening, is disposed furthest from the distal end of the distal portion of the outer conductor 560, and the fifth slot 505, which is the largest opening, is disposed closest to the distal end.

First, third and fifth slots 501, 503 and 505 longitudinally extend in a first direction at substantially the same angle relative to the longitudinal axis of the central conductor 520. Second and fourth slots 502 and 504 longitudinally extend in a second direction at substantially the same angle relative to the longitudinal axis of the central conductor 520. When the microwave signal propagates inside the leaky-wave antenna assembly 500, it "leaks" out through the first, second, third, fourth and fifth slots 501, 502, 503, 504 and 505, causing substantially uniform radiation along the longitudinal axis of the distal portion of the outer conductor 560.

Figure 6:
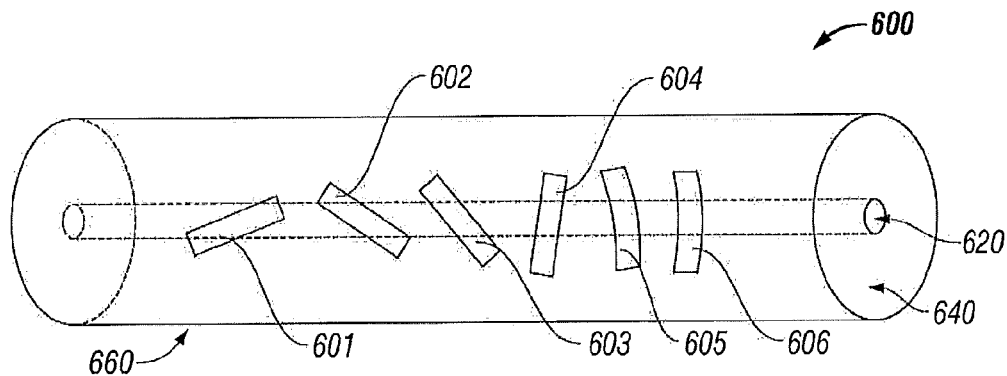
FIG. 6 is a perspective view of yet another embodiment of a leaky-wave antenna assembly according to the present disclosure.

FIG. 6 shows another embodiment of a leaky-wave antenna assembly and includes an inner conductor 620 and an outer conductor 660 coaxially surrounding the inner conductor 620. The distal portion of the outer conductor 660 is provided with a plurality of apertures for radiating energy. The apertures (referred to herein as the first, second, third, fourth, fifth and sixth slots 601, 602, 603, 604, 605 and 606) are configured for radiating energy substantially uniformly along the longitudinal axis of the outer conductor 660. In this embodiment, each of the first, second, third, fourth, fifth and sixth slots 601, 602, 603, 604, 605 and 606 are substantially the same size. Leaky-wave antenna assembly 600 may include a dielectric material 640 separating the inner conductor 620 and the outer conductor 660.

In the leaky-wave antenna assembly 600 shown in FIG. 6, each of the substantially equal-sized first, second, third, fourth, fifth and sixth slots 601, 602, 603, 604, 605 and 606 longitudinally extends at a different angle relative to the longitudinal axis of the central conductor 620. For example, the longitudinal axis of the sixth slot 606 extends substantially perpendicular to the longitudinal axis of the central conductor 620, whereas the longitudinal axis of the first slot 601 is near parallel to the longitudinal axis of the central conductor 620. As the microwave signal propagates inside the leaky-wave antenna assembly 600, it "leaks" out through the first, second, third, fourth, fifth and sixth slots 601, 602, 603, 604, 605 and 606, causing substantially uniform radiation along the longitudinal axis of the distal portion of the outer conductor 660.

Figure 7:
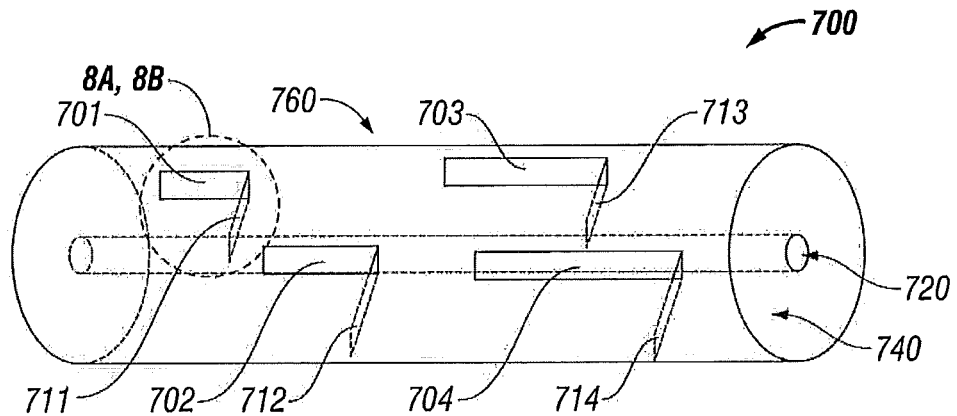
FIG. 7 is a perspective view of a leaky-wave antenna assembly configured with inclusion elements extending inwardly from the outer conductor according to an embodiment of the present disclosure.

FIG. 7 shows another embodiment of a leaky-wave antenna assembly and includes an inner conductor 720, an outer conductor 760 coaxially surrounding the inner conductor, a plurality of apertures (referred to herein as slots 701, 702, 703 and 704, respectively) for radiating energy, and may include a dielectric material 740 separating the inner and outer conductors. Leaky-wave antenna assembly 700 is similar to the leaky-wave antenna assembly 400 illustrated in FIG. 4, except that the leaky-wave antenna assembly 700 further includes inclusion elements 711, 712, 713 and 714 extending inwardly from the outer conductor 760. Each inclusion element 711, 712, 713 and 714 extends inwardly toward the inner conductor 720 at an angle relative to a plane substantially coextensive with the corresponding one of the slots 701, 702, 703 or 704.

Inclusion elements 711, 712, 713 and 714 each have a size, a shape, and an edge disposed substantially adjacent to an edge of a corresponding one of the slots 701, 702, 703 or 704. The size, shape and/or angle of each inclusion element 711, 712, 713 and 714 may be based on a wavelength of the energy to be radiated along the outer conductor 760. The size, shape and/or angle of each inclusion element 711, 712, 713 and 714 may be based on the location of the corresponding one of the slots 701, 702, 703 or 704 relative to the distal tip of the leaky-wave antenna assembly 700.

Figure 8A:
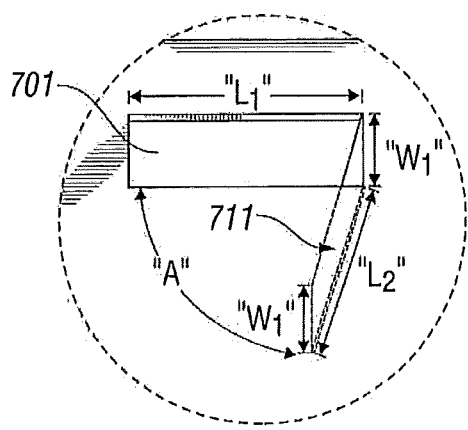
FIG. 8A is an enlarged view of the indicated area of detail of FIG. 7 according to an embodiment of the present disclosure.

FIG. 8A is an enlarged view of the slot 701 and the inclusion element 711 illustrated in FIG. 7 shown with example dimensions of the slot 701 and the inclusion element 711. The slot 701 has a length "L1" and a width "W1", and the inclusion element 711 has a length "L2" and a width "W1". The angle formed between the inclusion element 711 and a plane substantially coextensive with the corresponding one of the slot 701 is indicated by the arc labeled "A". In the leaky-wave antenna assembly 700 shown in FIG. 7, the inclusion elements 711, 712, 713 and 714 each have equal width "W1"; a first subset of the inclusion elements 711 and 713 have equal length "L2"; and a second subset of inclusion elements 712 and 714 have an equal length that is different than the length "L2" of the first set of inclusion elements. The lengths and widths of the apertures and inclusion elements may be varied from the configuration depicted in FIGS. 7 and 8A.

Figure 8B:
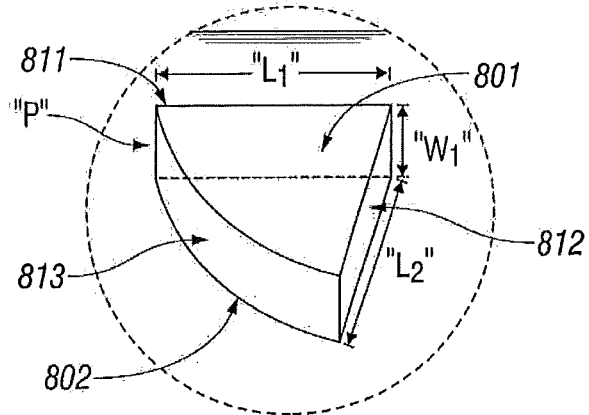
FIG. 8B is an enlarged view of the indicated area of detail of FIG. 7 according to another embodiment of the present disclosure.

FIG. 8B is an enlarged view of the slot 701 and the inclusion element 711 illustrated in FIG. 7 shown with a dielectric pocket "P" having an upper surface 801, a lower surface 802 opposed to the upper surface 801, a first side surface 811, a second side surface 812, and a third side surface 813. In the illustrated embodiment, the dielectric pocket "P" has a wedge-like shape, wherein each of the first and second side surfaces 811, 812 has a substantially rectangular shape with the first side surface 811 having a length "L1" and a width "W1" and the second side surface 812 having a length "L2" and a width "W1". The shape and volume of the dielectric pocket "P" may be varied from the configuration depicted in FIG. 8B.

Dielectric pocket "P" may be formed of material with a dielectric constant different than the dielectric constant of the dielectric material 740. For example, the dielectric pocket "P" may be formed of a material with a dielectric constant higher than the dielectric constant of the dielectric material 740, which may tend to concentrate more electric fields within the volume of the dielectric pocket "P". Dielectric pocket "P" may be formed of a material with a dielectric constant lower than the dielectric constant of the dielectric material 740, which may tend to lessen the electric fields within the volume of the dielectric pocket "P". Dielectric pocket "P" may be configured to assist in uniformity of leaky behavior of the leaky-wave antenna assembly 700. For example, respective widths of the inclusion elements may be larger, smaller and/or substantially equal to the width "W1" of the slots 701, 702, 703 and 704. It is contemplated herein that some apertures may not be provided with an inclusion element and/or some apertures may be provided with a plurality of inclusion elements. Inclusion elements may be integrally formed with the outer conductor 760, for example, by punching, bending and/or cutting of the material of the outer conductor 760, such that the apertures and the inclusion elements are commonly formed. Alternatively, the inclusion elements may be separately fabricated from any suitable electrically conductive materials and attached to an inner diametric surface of the outer conductor 760, e.g., by solder or adhesive.

Figure 9:
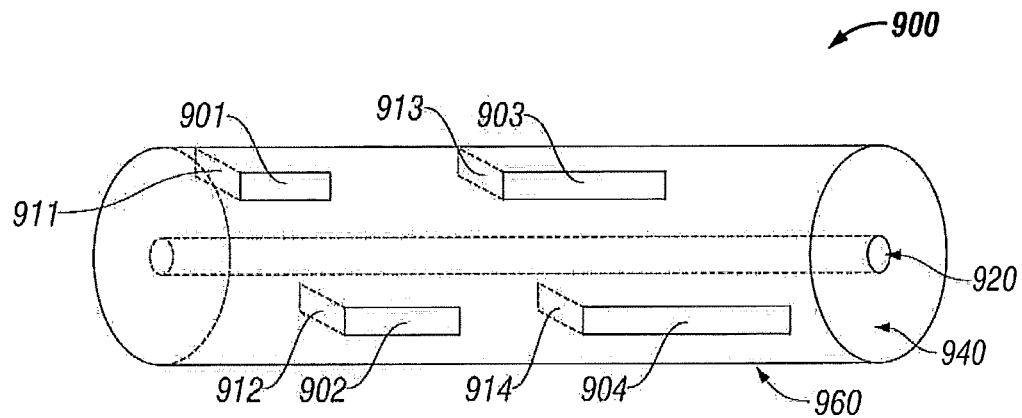
FIG. 9 is a perspective view of another embodiment of a leaky-wave antenna assembly configured with inclusion elements extending inwardly from the outer conductor according to the present disclosure.

FIG. 9 shows another embodiment of a leaky-wave antenna assembly and includes an inner conductor 920, an outer conductor 960 coaxially surrounding the inner conductor, and a plurality of apertures (referred to herein as first, second, third and fourth slots 901, 902, 903 and 904, respectively) for radiating energy. Leaky-wave antenna assembly 900 may include a dielectric material 940 separating the inner and outer conductors. Leaky-wave antenna assembly 900 is also similar to the leaky-wave antenna assembly 400 illustrated in FIG. 4, except that the leaky-wave antenna assembly 900 further includes inclusion elements 911, 912, 913 and 914 extending inwardly from the outer conductor 960. Inclusion elements 911, 912, 913 and 914 are similar to the inclusion elements 711, 712, 713 and 714 shown in FIG. 7, except that the inclusion elements 911, 912, 913 and 914 are respectively disposed substantially adjacent to a proximal edge of the slots 901, 902, 903 and 904, i.e., instead of a distal edge thereof as shown in FIG. 7. Leaky-wave antenna assembly 900 may include dielectric pockets (not shown), e.g., similar to the dielectric pocket "P" shown in FIG. 8B, which may be formed of a material with a dielectric constant different than the dielectric constant of the dielectric material 940.

Figure 10:
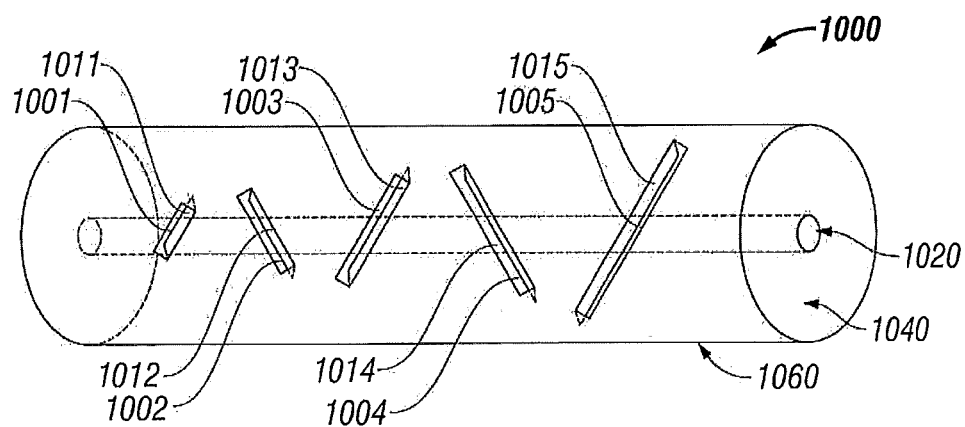
FIG. 10 is a perspective view of the leaky-wave antenna assembly illustrated in FIG. 5 shown with inclusion elements extending inwardly from the outer conductor according to an embodiment of the present disclosure.

FIG. 10 shows yet another embodiment of a leaky-wave antenna assembly and includes an inner conductor 1020, an outer conductor 1060 coaxially surrounding the inner conductor, and a plurality of apertures (herein referred to as first, second, third, fourth and fifth slots 1001, 1002, 1003, 1004 and 1005, respectively) for radiating energy, and may include a dielectric material 1040 separating the inner and outer conductors. Leaky-wave antenna assembly 1000 further includes a number of inclusion elements 1011, 1012, 1013, 1014 and 1015 extending inwardly from the outer conductor 1020. In this embodiment, the inclusion elements 1011, 1012, 1013 1014 and 1015 each have a different size.

In the leaky-wave antenna assembly 1000 shown in FIG. 10, each of the first, second, third, fourth and fifth slots 1001, 1002, 1003, 1004 and 1005 longitudinally extends at a different angle relative to the longitudinal axis of the central conductor 1020. A first subset of the inclusion elements 1011, 1012, 1013 and 1014, are respectively disposed substantially adjacent to a distal edge of the slots 1001, 1002, 1003 and 1004, and a second subset, i.e., inclusion element 1015, is disposed substantially adjacent to a proximal edge of the slot 1005. Leaky-wave antenna assembly 1000 may include dielectric pockets (not shown), e.g., similar to the dielectric pocket "P" shown in FIG. 8B, which may be formed of a material with a dielectric constant different than the dielectric constant of the dielectric material 1040.

Figure 11:
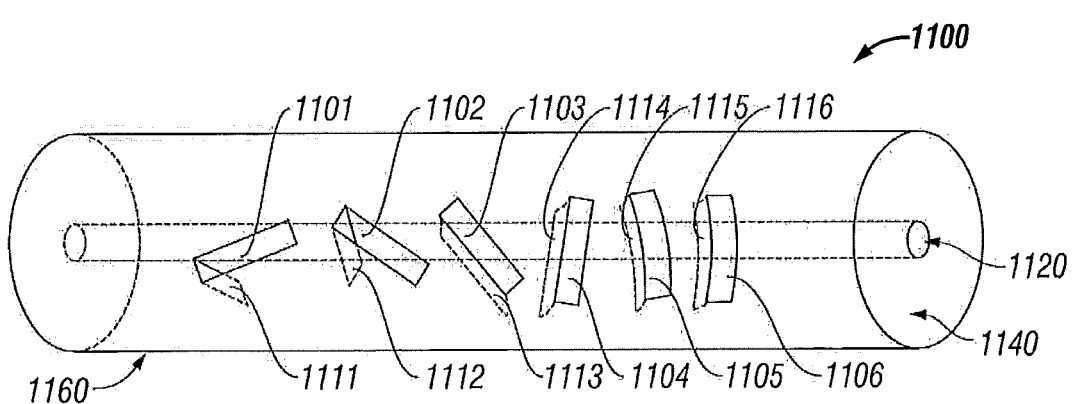
FIG. 11 is a perspective view of the leaky-wave antenna assembly illustrated in FIG. 6 shown with inclusion elements extending inwardly from the outer conductor according to an embodiment of the present disclosure.

FIG. 11 shows yet another embodiment of a leaky-wave antenna assembly and includes an inner conductor 1120, an outer conductor 1160 coaxially surrounding the inner conductor, and a plurality of apertures (referred to herein as slots 1101, 1102, 1103, 1104, 1105 and 1106, respectively) for radiating energy, and may include a dielectric material 1140 separating the inner and outer conductors. Leaky-wave antenna assembly 1100 further includes a number of inclusion elements 1111, 1112, 1113, 1114, 1115 and 1116 extending inwardly from the outer conductor 1120.

Each inclusion element 1111, 1112, 1113, 1114, 1115 and 1116 extends inwardly toward the inner conductor 1120 at an angle relative to a plane substantially coextensive with the slots 1101, 1102, 1103, 1104, 1105 and 1106, respectively. The size, shape and/or angle of each inclusion element 1111, 1112, 1113, 1114, 1115 and 1116 may be based on a wavelength of the energy to be radiated along the length of the outer conductor 1160. The size, shape and/or angle of each inclusion element 1111, 1112, 1113, 1114, 1115 and 1116 may be based on the location of the corresponding one of the slots 1101, 1102, 1103, 1104, 1105 and 1106 relative to the distal tip of the leaky-wave antenna assembly 700. As the microwave signal propagates inside the leaky-wave antenna assembly 1100, it "leaks" out through the slots 1101, 1102, 1103, 1104, 1105 and 1106, causing substantially uniform radiation along the longitudinal axis of the distal portion of the outer conductor 1160. Leaky-wave antenna assembly 1100 may include dielectric pockets (not shown), e.g., similar to the dielectric pocket "P" shown in FIG. 8B, which may be formed of a material with a dielectric constant different than the dielectric constant of the dielectric material 1140.

Figure 12A:
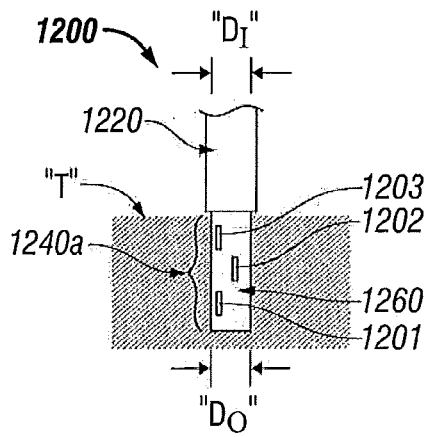
FIGS. 12A and 12B are schematic diagrams of a leaky-wave antenna assembly including a sleeve member according to an embodiment of the present disclosure.
Figure 12B:
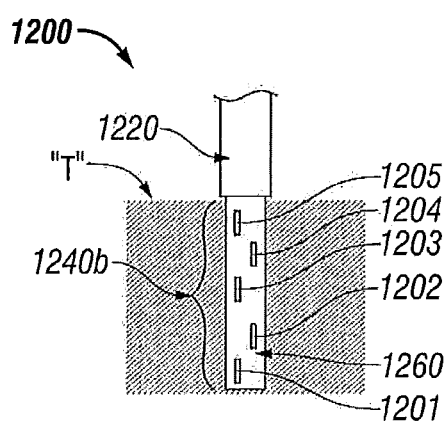

FIGS. 12A and 12B show a leaky-wave antenna assembly 1200 including a moveable sleeve member 1220 located at a periphery of the outer conductor 1260 coaxially with the outer conductor 1260. Sleeve member 1220 is adapted to be slideably moveable along the periphery of the leaky-wave antenna assembly 1200 between a first position, in which a first portion 1240A of the distal portion of the outer conductor 1260 is exposed, and a second position, in which a second portion 1240B larger than the first portion 1240A of the distal portion of the outer conductor 1260 is exposed. For example, when the sleeve member 1220 is in the first position shown in FIG. 12A, a first set of apertures 1201, 1202 and 1203, are exposed, and when the sleeve member 1220 is in the second position shown in FIG. 12B, a second set of apertures 1201, 1202, 1203, 1204 and 1205 are exposed. When the leaky-wave antenna assembly 1200 is operated with the sleeve member in the first position, the energy is applied to a first portion of the target volume of tissue "T", and when the leaky-wave antenna assembly 1200 is operated with the sleeve member 1220 in the second position, the energy is applied to a second portion larger than the first portion of the target volume of tissue "T".

Sleeve member 1220 shown in FIGS. 12A and 12B is a substantially cylindrical shaped structure having an inner diameter "DI", which is larger than an outer diameter "DO" of the outer conductor 1260. The sleeve member 1220 is slideably movable to various positions such that any suitable number of apertures may be exposed. The number of apertures to be exposed may be based on various factors, such as, for example, the volume of target tissue to be treated, the desired procedure, the wavelength of the energy to be radiated, and the shape and dimensions of the apertures.

Figure 13:
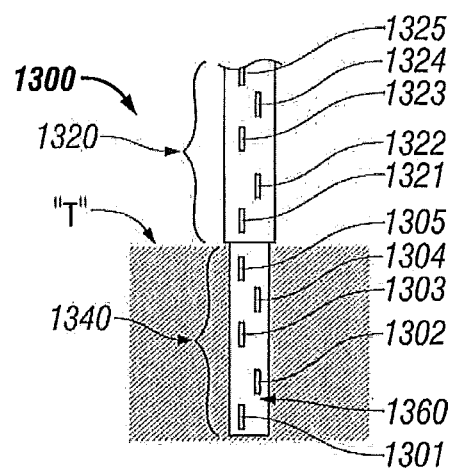
FIG. 13 is a schematic diagram of a leaky-wave antenna assembly including a sleeve member according to another embodiment of the present disclosure.

FIG. 13A shows a leaky-wave antenna 1300 including a moveable sleeve member 1320 located at a periphery of the outer conductor 1360 coaxially with the outer conductor 1360. Sleeve member 1320 is adapted to be rotationably moveable and slideably moveable along the periphery of the leaky-wave antenna assembly 1300 to various positions or various rotation positions to vary slot openings with rotation angle. Sleeve member 1320 includes a plurality of apertures 1321, 1322, 1323, 1324 and 1325 and can be positioned relative to the outer conductor 1360 such that any suitable number of slot openings may be exposed. For example, the sleeve member 1320 is moveable such that the apertures 1321, 1322, 1323, 1324 and 1325 are respectively positioned in alignment with the slots 1301, 1302, 1303, 1304 and 1305 in the outer conductor 1360 to create leaky-wave openings. The number, shape and pattern of apertures in the sleeve member 1320 may be varied from the configuration depicted in FIG. 13 and may be selectable by a user, e.g., for a particular antenna deposition pattern.

Figure 14:
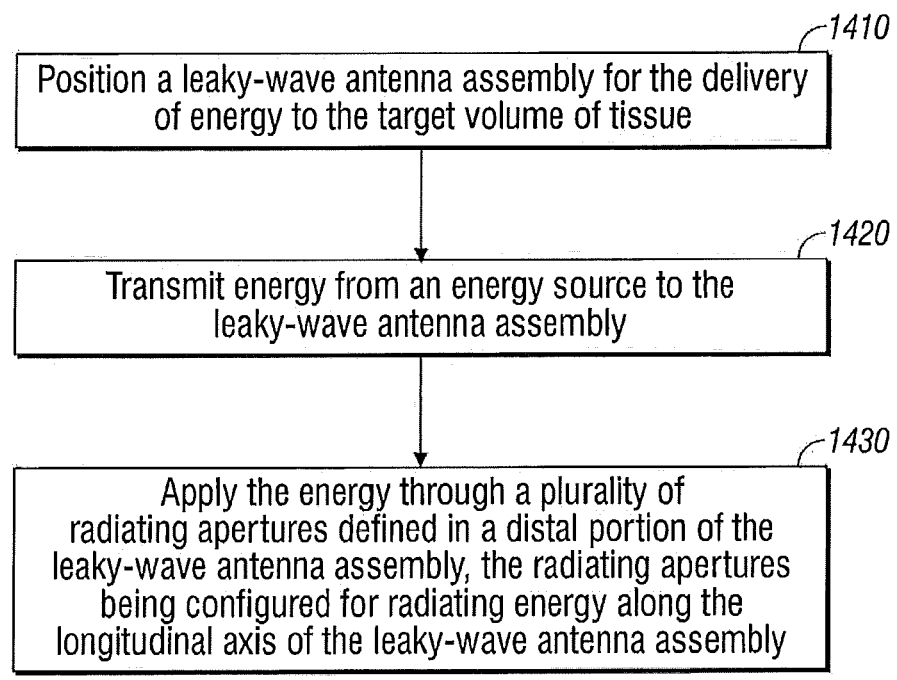
FIG. 14 is a flowchart illustrating a method of directing energy to a target volume of tissue according to an embodiment of the present disclosure.

FIG. 14 is a flowchart illustrating a method of directing energy to a target volume of tissue. In step 1410, a leaky-wave antenna assembly, e.g., 400, is positioned for the delivery of energy to the target volume of tissue. Leaky-wave antenna assembly 400 may be inserted directly into tissue (e.g., as shown in FIGS. 12A and 12B), inserted through a lumen, e.g., a vein, needle or catheter, placed into the body during surgery by a clinician, or positioned in the body by other suitable methods known in the art.

In step 1420, energy from an energy source is transmitted to the leaky-wave antenna assembly. For example, the energy source may be any suitable electrosurgical generator for generating an output signal. In one embodiment, the energy source is a microwave energy source.

In step 1430, the energy is applied through a plurality of radiating apertures, e.g., 401, 402, 403 and 404, in a distal portion of the leaky-wave antenna assembly. The radiating apertures 401, 402, 403 and 404 are configured for radiating energy along the longitudinal axis of the leaky-wave antenna assembly 400. For example, the size and/or the angle of each aperture relative to the inner conductor 420 of the leaky-wave antenna assembly 400 may be varied in relation to the other apertures such that the energy radiated along the leaky-wave antenna assembly 400 is substantially uniform. For example, at least a subset of the radiating apertures may extend at different angles relative to the longitudinal axis of the leaky-wave antenna assembly. The size and/or the angle of each aperture relative to the inner conductor 420 may be varied in relation to the other apertures such that the energy radiated along the leaky-wave antenna assembly 400 may have a substantially pear shape, hour-glass shape or other shape.

Figure 15:
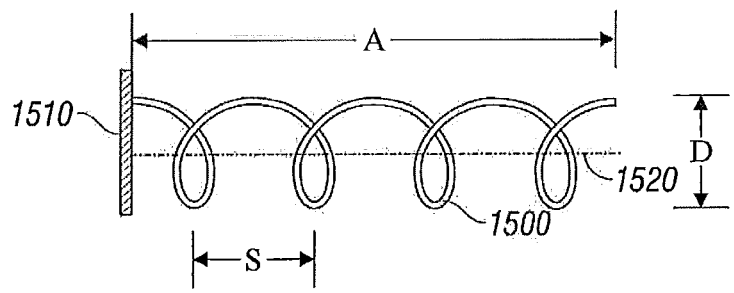
FIG. 15 is a schematic diagram showing the basic geometry of a helical antenna.

A typical helical antenna is illustrated in FIG. 15 and includes a conducting wire 1500 that is coiled to form a helix having an axis 1520 and backed by a conducting ground plane 1510. The basic geometrical parameters that define a helical antenna include the diameter D and circumference C of the helix, where $C=\pi D$, the number of turns N of the helix, the center-to-center spacing S between turns, the pitch angle $\alpha$, where $\alpha = \arctan(S/\pi D)$, and the axial length A of the helix, where $A=N \times S$. When the circumference of the helix is small compared with the axial length and the wavelength, the helical antenna radiates in the normal mode (similar to dipole antenna radiation). When the helix circumference is about one wavelength, the helical antenna operates in the axial mode. Typically, a helical antenna radiates in the normal mode when $C<0.4\lambda$ ($\lambda$ is the wavelength) and in the axial mode for approximately $0.75\lambda < C < 1.3\lambda$.

Figure 16:
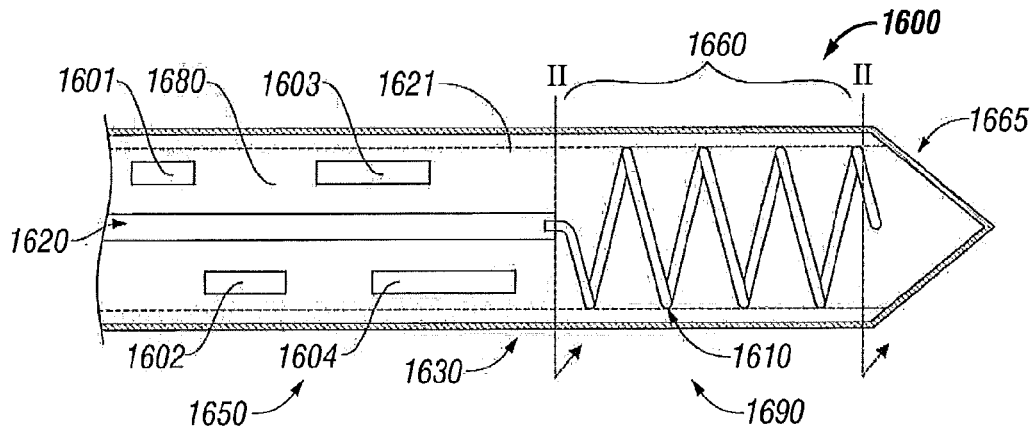
FIG. 16 is a schematic diagram showing a dual antenna assembly including a leaky-wave antenna assembly and a helical antenna assembly according to an embodiment of the present disclosure.

FIG. 16 shows an embodiment of a dual antenna assembly including a leaky-wave antenna assembly and a helical antenna assembly. The leaky-wave antenna assembly 1650 shown in FIG. 16 is similar to the leaky-wave antenna assembly 400 of FIG. 4 and further description thereof is omitted in the interests of brevity. The helical antenna assembly 1690 shown in FIG. 16 includes a helical antenna radiating section 1660 and a tip portion 1665. Tip portion 1665 is configured for penetrating tissue. Although the surfaces of the tip portion 1665 shown in FIG. 16 are generally flat, the surfaces of the tip portion 1665 according to various embodiments may be curved or may include a combination of flat, sloped or curved portions. The shape and size of the tip portion 1665 may be varied from the configuration depicted in FIG. 16. The helical antenna radiating section 1660 includes a helical antenna element 1610.

Figure 17:
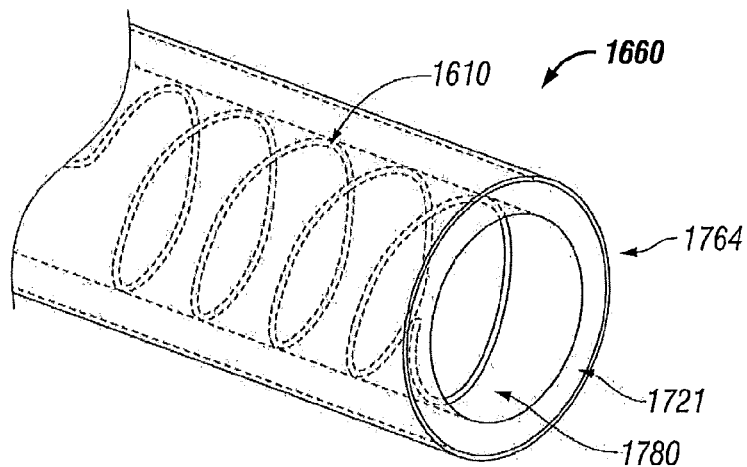
FIG. 17 is a perspective view of a portion of the helical antenna assembly shown in FIG. 16 taken along the lines II-II.

FIG. 17 shows a portion of the helical antenna assembly of FIG. 16 taken along the lines II-II. Referring to FIG. 17, the helical antenna radiating section 1660 includes a distal end 1764. Helical antenna assembly 1600 can be operated in the axial mode to perform a procedure on a first portion of a target volume of tissue, wherein the first portion of the tissue is located distal to end 1764 of the helical antenna assembly 1600. Helical antenna assembly 1600 can be operated in the normal mode to perform a second procedure on a second portion of the target volume of tissue, wherein the second portion is located substantially adjacent to the helical antenna radiating section 1660. Various sequences of axial and normal modes of operation may be utilized depending on the particular application of the helical antenna assembly 1600.

The helical antenna radiating section 1660 further includes a sleeve portion 1721 located at the periphery of the helical antenna element 1610 coaxially with the helical antenna element 1610, and a cavity 1780 located to the interior of the helical antenna element 1610. In an embodiment, the sleeve portion 1721 is formed of a dielectric material and may include a material that has variable dielectric constant, or adjustable dielectric constant, so that effective wavelengths will vary between the axial mode and the normal mode of operation.

Figures 18, 19:
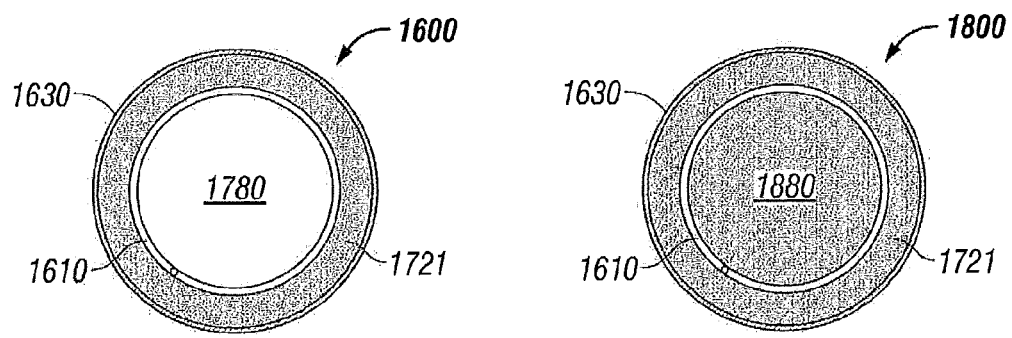
FIG. 18 is a cross-sectional view of the helical antenna radiating section shown in FIG. 17.
FIG. 19 is a cross-sectional view of the helical antenna radiating section of FIG. 17 shown with a dielectric material located in an interior of the helical antenna element according to an embodiment of the present disclosure.

FIG. 18 is a cross-sectional view of the helical antenna radiating section 1660 of FIG. 17. FIG. 18 shows the helical antenna radiating section 1660 including the helical antenna element 1610 enclosed by a first dielectric material 1721. First dielectric material 1721 may include ferroelectric dielectric materials, which through applied DC voltage may allow control of the depth and spread of the power deposition pattern.

FIG. 19 is a cross-sectional view of the helical antenna radiating section of FIG. 17 shown with a dielectric material located in an interior of the helical antenna element. Helical antenna radiating section 1800 is similar to the helical antenna radiating section 1600 shown in FIG. 18, except that the helical antenna radiating section 1800 includes a second dielectric material 1880 disposed to the interior of the helical antenna element 1610, i.e., instead of the cavity 1780. Second dielectric material 1880 may include ferroelectric dielectric materials.

Figure 20:
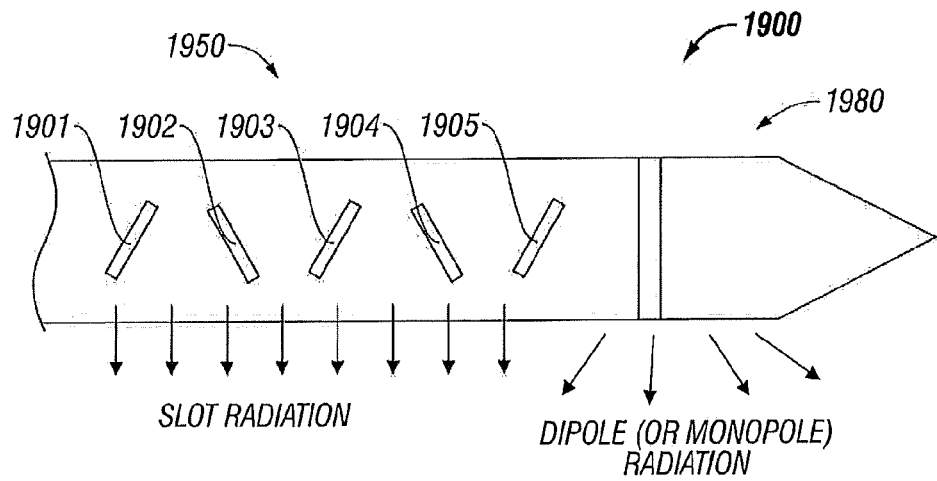
FIG. 20 is a schematic diagram showing a dual antenna assembly according to an embodiment of the present disclosure.

FIG. 20 shows another embodiment of a dual antenna assembly. The dual antenna assembly 1900 illustrated in FIG. 20 includes a proximal portion 1950 and a distal portion 1980. Proximal portion 1950 includes a leaky-wave antenna assembly having a plurality of slots 1901, 1902, 1903, 1904 and 1905. Distal portion 1980 includes either a dipole or monopole antenna assembly. The arrows in FIG. 20 show the leaky radiation along the proximal portion 1950 and the dipole (or monopole) radiation on the distal portion 1980.

Figure 21:
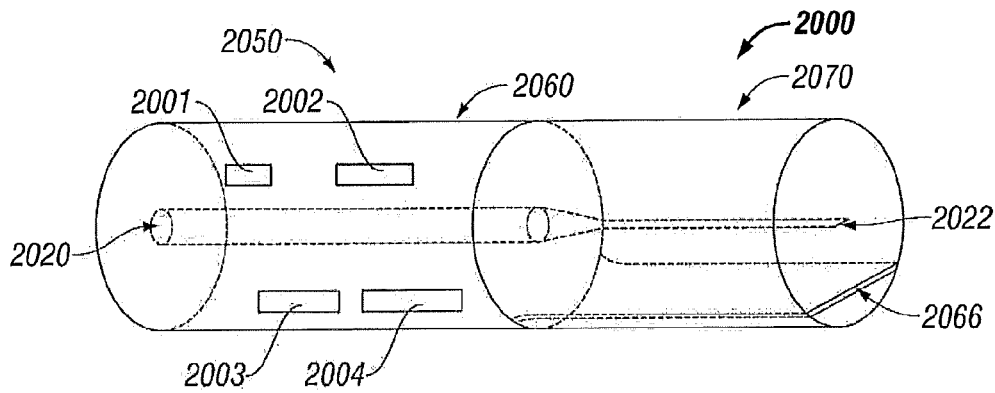
FIG. 21 is a perspective view of a dual antenna assembly including a leaky-wave antenna assembly and a microstrip antenna assembly according to an embodiment of the present disclosure.

FIG. 21 shows yet another embodiment of a dual antenna assembly. Dual antenna assembly 2000 includes a leaky-wave antenna assembly 2050 and a microstrip antenna assembly 2070. Leaky-wave antenna assembly 2050 includes an outer conductor 2060, which is provided with a plurality of slots 2001, 2002, 2003 and 2004 for radiating energy, and an inner conductor 2020. Microstrip antenna assembly 2070 includes a lower conductor 2066, which is electrically connected to the outer conductor 2060 of the leaky-wave antenna assembly 2050, and a central conductor 2022, which is electrically connected to the inner conductor 2020 of the leaky-wave antenna assembly 2050.

Figure 22:
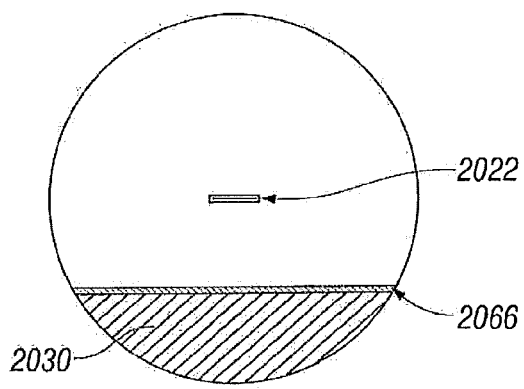
FIG. 22 is a cross-sectional view of the distal portion of the dual antenna assembly of FIG. 21.

FIG. 22 is a cross-sectional view of the distal portion of the dual antenna assembly illustrated in FIG. 21. As shown in FIG. 22, a dielectric material 2030 is disposed adjacent to the lower conductor 2066.

Figure 23:
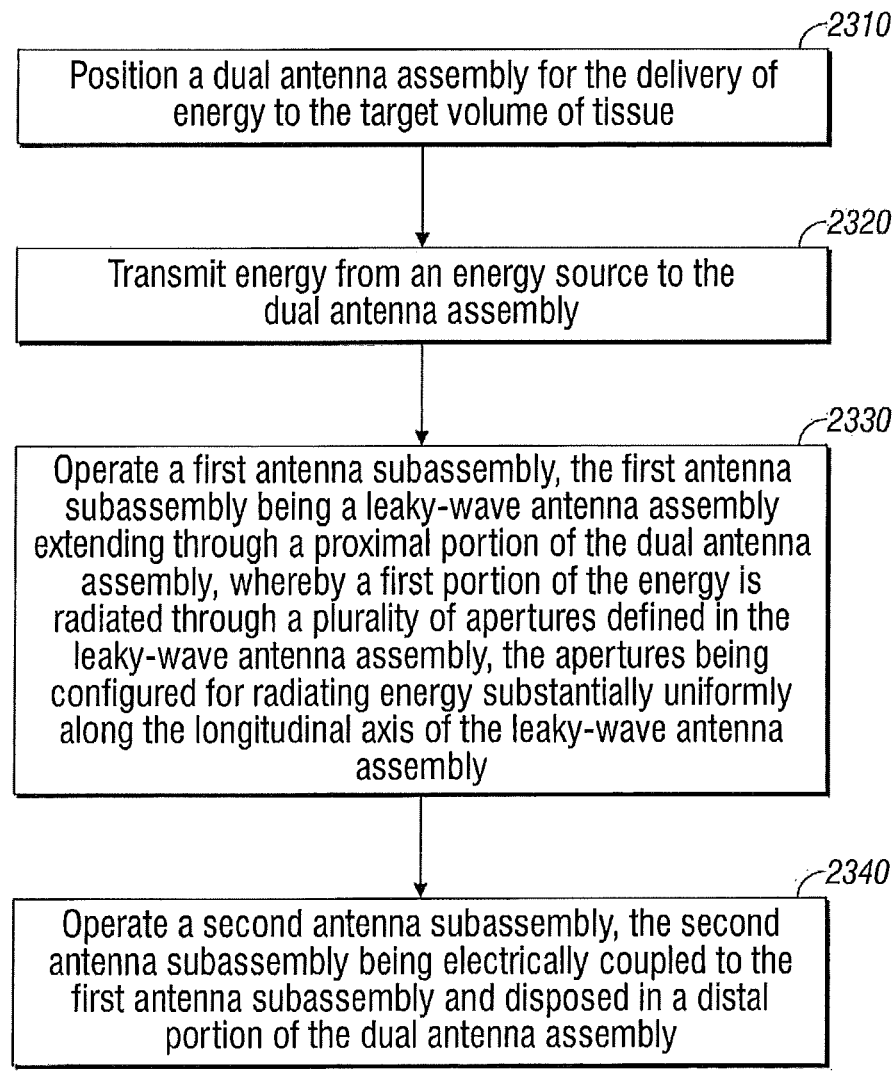
FIG. 23 is a flowchart illustrating a method of directing energy to a target volume of tissue according to an embodiment of the present disclosure.

FIG. 23 is a flowchart illustrating a method of directing energy to a target volume of tissue. In step 2310, a dual antenna assembly, e.g., 1600, is positioned for delivery of energy to the target volume of tissue.

In step 2320, energy from an energy source is transmitted to the dual antenna assembly 1600. The energy source may be an electrosurgical generator for generating an output signal. In one embodiment, the energy source is a microwave energy source.

In step 2330, a first antenna subassembly is operated, the first antenna subassembly being a leaky-wave antenna assembly, e.g., 400, extending through a proximal portion of the dual antenna assembly, whereby a first portion of the energy is radiated through a plurality of apertures in the leaky-wave antenna assembly 400, the apertures being configured for radiating energy substantially uniformly along a longitudinal axis of the leaky-wave antenna assembly 400.

In step 2340, a second antenna subassembly, e.g., 1660, is operated, the second antenna subassembly 1660 being electrically coupled to the first antenna subassembly 400 and disposed in a distal portion of the dual antenna assembly 1600.

In various embodiments of the presently disclosed leaky-wave antenna assemblies, uniform radiation with a leaky-wave coaxial cable is achieved by compensating for signal attenuation along the cable (stronger signal proximally, close to generator, and weaker signal distally) by varying slots size and/or slot direction so that smaller slots and/or slots angled more parallel to the cable axis are placed proximally (where the signal is stronger), while larger slots and/or slots transverse to the cable axis are placed distally (where the signal has been attenuated more), with gradual change in slot size and/or direction in between.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing exemplary embodiments may be made without departing from the scope of the disclosure.

What is claimed is:

1. A device for directing energy to tissue, comprising:
an inner conductor having a length;
an outer conductor coaxially surrounding the inner conductor along at least a portion of the length, the outer conductor having a proximal portion and a distal portion, the distal portion of the outer conductor including a plurality of conductor apertures defined therein; and
a plurality of inclusion elements disposed substantially adjacent to an edge of a corresponding one of the conductor apertures, each inclusion element extending beyond the edge of a corresponding one of the conductor apertures and inwardly toward the inner conductor at an angle relative to a plane substantially coextensive with the corresponding one of the conductor apertures.

2. The device according to claim 1, wherein each of the conductor apertures has a size and extends at an angle relative to a longitudinal axis of the outer conductor and at least one of the size and the angle of each conductor aperture is varied in relation to the other conductor apertures.

3. The device according to claim 2, wherein the sleeve member includes a plurality of sleeve apertures.

4. The device according to claim 3, wherein the sleeve member is movable between a first position in which the plurality of sleeve apertures are substantially aligned with the plurality of conductor apertures and a second position in which at least a portion of the plurality of conductor apertures is enclosed by the sleeve member.

5. The device according to claim 1, further comprising:
a sleeve member coaxially disposed about the outer conductor, wherein the sleeve member is at least one of rotationally or longitudinally moveable relative to the outer conductor.

6. The device according to claim 1, wherein the energy radiated from each conductor aperture is substantially the same.

7. The device according to claim 1, wherein each of the inclusion elements has a size, a shape and at least one of the size, the shape, and the angle of each inclusion element is based on a wavelength of the energy radiated along the inner and outer conductors.

8. The device according to claim 7, wherein at least one of the size, the shape, and the angle of each inclusion element is based on a distance of the corresponding one of the conductor apertures relative to a distal tip of the device.

9. The device according to claim 8, further comprising:
a first dielectric material disposed between the inner and outer conductors, the first dielectric material having a first dielectric constant.

10. The device according to claim 9, wherein each of the inclusion elements includes a second dielectric material having a second dielectric constant different than the first dielectric constant.

11. A system for directing energy to tissue, comprising:
a source of microwave energy configured to generate microwave energy; and
a leaky-wave antenna assembly coupled to the source of microwave energy, the leaky-wave antenna assembly including:
an inner conductor having a length;
an outer conductor coaxially surrounding the inner conductor along at least a portion of the length, the outer conductor having a proximal portion and a distal portion, the distal portion of the outer conductor including a plurality of conductor apertures defined therein; and
a plurality of inclusion elements disposed substantially adjacent to an edge of a corresponding one of the conductor apertures, each inclusion element extending beyond the edge of a corresponding one of the conductor apertures and inwardly toward the inner conductor at an angle relative to a plane substantially coextensive with the corresponding one of the conductor apertures.

12. The system according to claim 11, wherein each of the conductor apertures has a size and extends at an angle relative to a longitudinal axis of the outer conductor and at least one of the size and the angle of each conductor aperture is varied in relation to the other conductor apertures such that the microwave energy radiated along the inner and outer conductors is substantially the same.

13. The system according to claim 11, wherein each of the inclusion elements has a size, a shape and at least one of the size, the shape, and the angle of each inclusion element is based on a wavelength of the microwave energy radiated along the inner and outer conductors.

14. The system according to claim 11, wherein at least one of the size, the shape, and the angle of each inclusion element is based on a distance of the corresponding one of the conductor apertures relative to a distal tip of the device.

15. The system according to claim 11, further comprising:
a transmission line having proximal and distal ends and configured to transmit the microwave energy, wherein the proximal end of the transmission line is coupled to the source of microwave energy and the distal end of the transmission line is coupled to a proximal end of the leaky-wave antenna assembly.

16. A method for directing energy to tissue, comprising:
positioning a leaky-wave antenna assembly adjacent to or within the tissue, the leak-wave antenna assembly including a distal portion configured to emit energy in a radiation pattern and a sleeve member coaxially and slidably disposed about the outer conductor;
transmitting energy from an energy source to the leaky-wave antenna assembly;
applying the energy through a plurality of radiating apertures defined in a distal portion of the leaky-wave antenna assembly; and
moving the sleeve member in at least one of rotational or longitudinal displacement relative to the distal portion to adjust the radiation pattern.

17. The method according to claim 16, wherein the distal portion includes a plurality of conductor apertures defined therein.

18. The method according to claim 17, wherein the leaky-wave antenna assembly includes a plurality of inclusion elements disposed substantially adjacent to an edge of a corresponding one of the conductor apertures, each inclusion element extending beyond the edge of a corresponding one of the conductor apertures and inwardly toward the inner conductor at an angle relative to a plane substantially coextensive with the corresponding one of the conductor apertures.

19. The method according to claim 17, wherein the sleeve member includes a plurality of sleeve apertures.

20. The method according to claim 19, wherein moving the sleeve member further includes moving the sleeve between a first position in which the plurality of sleeve apertures are substantially aligned with the plurality of conductor apertures and a second position in which at least a portion of the plurality of conductor apertures are enclosed by the sleeve.

* * * * *